US009415051B1

(12) United States Patent
Raud et al.

(10) Patent No.: US 9,415,051 B1
(45) Date of Patent: Aug. 16, 2016

(54) USE OF PEMIROLAST

(71) Applicant: RSPR Pharma AB, Stockholm (SE)

(72) Inventors: Johan Raud, Stockholm (SE); Carl-Johan Dalsgaard, Stockholm (SE); Göran Tornling, Enebyberg (SE)

(73) Assignee: RSPR Pharma AB, Stockholm (SE)

( * ) Notice: Subject to any disclaimer, the term of this patent is extended or adjusted under 35 U.S.C. 154(b) by 0 days.

(21) Appl. No.: 14/951,202

(22) Filed: Nov. 24, 2015

(30) Foreign Application Priority Data

Oct. 23, 2015  (GB) .................................. 1518831.1

(51) Int. Cl.
*A61K 31/519* (2006.01)
*C07D 487/04* (2006.01)

(52) U.S. Cl.
CPC ............ *A61K 31/519* (2013.01); *C07D 487/04* (2013.01); *Y10S 514/826* (2013.01)

(58) Field of Classification Search
None
See application file for complete search history.

(56) References Cited

U.S. PATENT DOCUMENTS 4,122,274 A    10/1978    Juby

FOREIGN PATENT DOCUMENTS

| EP | 0316174 A1 | 5/1989 |
| EP | 1285921 A1 | 2/2003 |
| WO | 2010146348 A2 | 12/2010 |

OTHER PUBLICATIONS

"Guidance for Industry: Estimating the Maximum Safe Starting Dose in Initial Clinical Trials for Therapeutics in Adult Healthy Volunteers", US FDA, Center for Drug Evaluation and Research, Jul. 2005, pp. 1-27.*
Roquet et al., "Combined Antagonism of Leukotrienes and Histamine Produces Predominant Inhibition of Allergen-Induced Early and Late Phase Airway Obstruction in Asthmatics," Am. J. Respir. Crit. Care Med. 155:1856-63 (1997).
Beasley et al., "Effect of a Thromboxane Receptor Antagonist on PGD2- and Allergen-Induced Bronchoconstriction," J. Appl. Physiol. 66:1685-93 (1989).
Dogné et al., "Therapeutic Potential of Thromboxane Inhibitors in Asthma," Expert Opin. Investig. Drugs 11(2):275-81 (2002).
Mathé et al., "Bronchial Hyperreactivity to Prostaglandin F2α and Histamine in Patients with Asthma," British Medical Journal 1:193-96 (1973).
Knight et al., "Histamine-Induced Contraction of Human Isolated Bronchus is Enhanced by Endogenous Prostaglandin F2α and Activation of TP Receptors," Eur. J. Pharmacol. 319:261-67 (1997).
Armour et al., "Characterization of Contractile Prostanoid Receptors on Human Airway Smooth Muscle," Eur. J. Pharmacol. 165:215-22 (1989).
Ninomiya et al., "General Pharmacological Study of TBX," Japanese Pharmacology and Therapeutics 17(4):121-51 (1989).
Deshpande et al., "Bitter Taste Receptors on Airway Smooth Muscle Bronchodilate by Localized Calcium Signaling and Reverse Obstruction," Nature Medicine 16(11):1299-1305 (2010).
Pharmaceutical Interview Form (IF)—Alegysal (2007).
Yoshida et al., "Clinical Evaluation of an Oral Antiallergic Agent, TBX Tablet, in Adult Bronchial Asthma: A Multi-Center, Double-Blind Study in Comparison with Tranirast," Japanese Pharmacology & Therapeutics 17(3):1-61 (1989) (English translation only).
Brannan et al., "Evidence of Mast Cell Activation and Leukotriene Release After Mannitol Inhalation," Eur. Respir. J. 22:491-6 (2003).
Busse, W.W., "The Relationship of Airway Hyperresponsiveness and Airway Inflammation. Airway Hyperresponsiveness in Asthma: Its Measurement and Clinical Significance," Chest 138(2):4S-10S (2010).
"Pemirolast Potassium," Drugs of Today, 28(1):29-31 (1992).
Hardy et al., "The Bronchoconstrictor Effect of Inhaled Prostaglandin D2 in Normal and Asthmatic Men," The New England Journal of Medicine 311(4):209-13 (1984).
Hasegawa et al., "Kinetic Interaction Between Theophylline and a Newly Developed Anti-Allergic Drug, Pemirolast Potassium," Eur. J. Clin. Pharmacol. 46:55-58 (1994).
Kemp et al., "Pemirolast, A New Oral Nonbrochodilator Drug for Chronic Asthma," Annals of Allergy 68:488-92 (1992).
Kurosawa, M., "Anti-Allergic Drug Use in Japan—The Rationale and the Clinical Outcome," Clinical and Experimental Allergy 24:299-306 (1994).
Leuppi, J.D., "Bronchoprovocation Tests in Asthma: Direct Versus Indirect Challenges," Curr. Opin. Pulm. Med. 20:31-6 (2014).
Taniguchi et al., "Antigen-Induced Airway Hyperresponsiveness in Infantile Guinea Pigs," Arerugi 47(8):720-5 (1998) (English abstract only).
Yanagihara et al., "Immunopharmacological Studies on TBX, a New Antiallergic Drug (1) Inhibitory Effects on Passive Cutaneous Anaphylaxis in Rats and Guinea Pigs," Japan J. Pharmacol. 48:91-101 (1988).
Yanagihara et al., "Immunopharmacological Studies on TBX, a New Antiallergic Drug (3) Inhibitory Effects on Histamine Release from Lung Fragments and Bronchoconstriction in Guinea Pigs," Japan J. Pharmacol. 51:83-92 (1989).
Taniguchi et al., "Antigen-Induced Airway Hyperresponsiveness in Infantile Guinea Pigs," Arerugi 47(8):720-5 (1998) (full article with English translation).

* cited by examiner

*Primary Examiner* — James D Anderson
*Assistant Examiner* — Gregg Polansky
(74) *Attorney, Agent, or Firm* — LeClairRyan, a Professional Corporation

(57) ABSTRACT

According to the invention there is provided a method for the treatment of airway hyperresponsiveness, which method comprises the administration of pemirolast, or a pharmaceutically acceptable salt thereof, to a patient in need of such treatment. Suitable lower doses of pemirolast are least about 110 mg per day.

7 Claims, 3 Drawing Sheets

USE OF PEMIROLAST

This application claims priority benefit of GB 1518831.1, filed Oct. 23, 2015.

FIELD OF THE INVENTION

This invention relates to a new pharmaceutical use.

BACKGROUND AND PRIOR ART

Asthma is one of the most common chronic inflammatory diseases, known to affect nearly 25 million citizens in the US alone. In childhood, it is the most common chronic disease, affecting in the region of an estimated 7 million US children.

The pathophysiology of asthma is complex and involves airway inflammation, intermittent airflow obstruction, and bronchial (airway) hyper-responsiveness, resulting in shortness of breath, wheezing, coughing, chest tightness and/or pain, as well as other non-specific symptoms in young children, including recurrent bronchitis, bronchiolitis, or pneumonia and the like.

Diagnosis may be made under guidelines from the (US) National Asthma Education and Prevention Program and include prevalence of episodic symptoms of airflow obstruction and/or at least partially reversible airflow obstruction or symptoms, followed by spirometry with post-bronchodilator response, and/or chest radiography (mainly to rule out other pulmonary diseases), as more definitive diagnostic tools.

There is presently no cure for asthma, and treatments often revolve around avoidance of known triggers, such as allergens, dust, pollutants, etc.

In the management and/or treatment of asthma, the ultimate goal is to prevent symptoms, minimize morbidity and prevent functional and psychological morbidity to provide a healthy (or near healthy) lifestyle.

However, there is also a need to reduce the numerical frequency and severity of acute asthma episodes. Such acute exacerbations of asthma are usually commonly referred to as "asthma attacks". Symptoms include shortness of breath, wheezing, and tightness in the chest. In severe cases, breathing may be significantly impaired such that the condition may become life-threatening.

Acute asthma attacks can often be brought on by infections, allergens, air pollution, exercise or insufficient or inappropriate medication use.

The most commonly-used active agents are presently employed to prevent asthma episodes ("preventers"). Such medications make the airways less sensitive, reduce airway inflammation and help to dry up mucus. Such preventers need to be taken every day to prevent symptoms and asthma attacks, and it may take a few weeks before they reach their full effect. Preventer medications include long-acting bronchodilators, oral theophylline, inhaled corticosteroids, leukotriene modifiers, cromones (cromolyn or nedocromil) and anti-IgE antibodies.

On the other hand, relief medications ("relievers") are fast acting medications that give quick relief of existing asthma symptoms or "attacks" (wheeze, cough, shortness of breath). They are bronchodilators, which means that they relax the muscle around the outside of the airway, which opens the airway. Every asthmatic patient should have a reliever medication. There are three main categories of reliever medication: theophylline; short-acting beta-agonists, such as terbutaline and salbutamol; and anticholinergics, such as ipratropium.

A more severe condition, known as status asthmaticus or acute severe asthma, is an acute exacerbation of asthma that does not respond well to such standard treatments.

Additionally, there are drawbacks associated with all of the aforementioned drugs (particularly inhaled corticosteroids), including lack of efficacy, non-adherence to treatment regimens, tolerance dependence and safety profiles/side-effects. Accordingly, there is thus a real clinical need for safer and/or more effective treatments of asthma. There is also presently a clinically-unmet need for effective treatments of airway or bronchial hyperresponsiveness.

Pemirolast is an orally-active anti-allergic mast cell inhibitor that is used in the prevention of conditions such as asthma, allergic rhinitis and conjunctivitis. See, for example, U.S. Pat. No. 4,122,274, European Patent Applications EP 316 174 and EP 1 285 921 and *Drugs of Today*, 28, 29 (1992). The drug is only known for the prophylaxis (i.e. preventative treatment) of asthma, and indeed has been marketed for over 20 years in e.g. Japan as the potassium salt in 5 and 10 mg doses (equating to 4.25 and 8.5 mg of the free acid, respectively) e.g. under the trademark ALEGYSAL™. Two doses are administered every day to provide an immediate mast cell stabilising effect and so the short-term prevention of asthma attacks resulting from subsequent challenge by the aforementioned asthma triggers.

In 1992, Kemp et al published the results of study in which pemirolast was said to have no effect whatsoever on airway or bronchial hyperresponsiveness (see *Annals of Allergy*, 68, 488 (1992)) when 50 mg doses were used twice daily in humans.

SUMMARY OF THE INVENTION

We have previously found that pemirolast has a previously-undisclosed and unappreciated plasma concentration (exposure) profile which means that it can be employed safely in doses that are significantly higher than those presently employed in the prevention of asthma.

In a double-blind, randomised clinical trial with a primary objective to investigate the relative efficacy of high dose and low dose pemirolast versus placebo in the prevention of the severity of mannitol-induced asthma attacks in human asthmatic subjects, a highly surprising and unexpected effect was observed.

In particular, patients having previously received high dose pemirolast were found to be "protected" from bronchoconstriction during mannitol challenge, several days after that high dose had been administered, when there was no pemirolast remaining in plasma to provide its known short-term/ immediate biological effect as a mast cell stabiliser.

In other words, subjects being administered placebo were found to be less responsive to an attempted mannitol-induced asthma attack only after having been administered a high dose of pemirolast, several days previously.

This means that high doses of pemirolast are surprisingly capable of affecting positively underlying airway hyperresponsivess in asthmatic patients. This is thought to occur by way of an unknown mechanism that has nothing to do with pemirolast's understood mechanism of action as a mast cell stabiliser. (For example, Yanagihara et al have reported (in *Japan J. Pharmacol.*, 48, 91 (1988)) that, after peroral administration of currently-employed clinical doses, pemirolast ceases to have a protective effect against IgE-induced passive cutaneous anaphylaxis (and therefore no mast cell stabilising/ inhibitory effect) as little as 240 minutes (i.e. 4 hours) after administration.)

DISCLOSURE OF THE INVENTION

Figure 1:
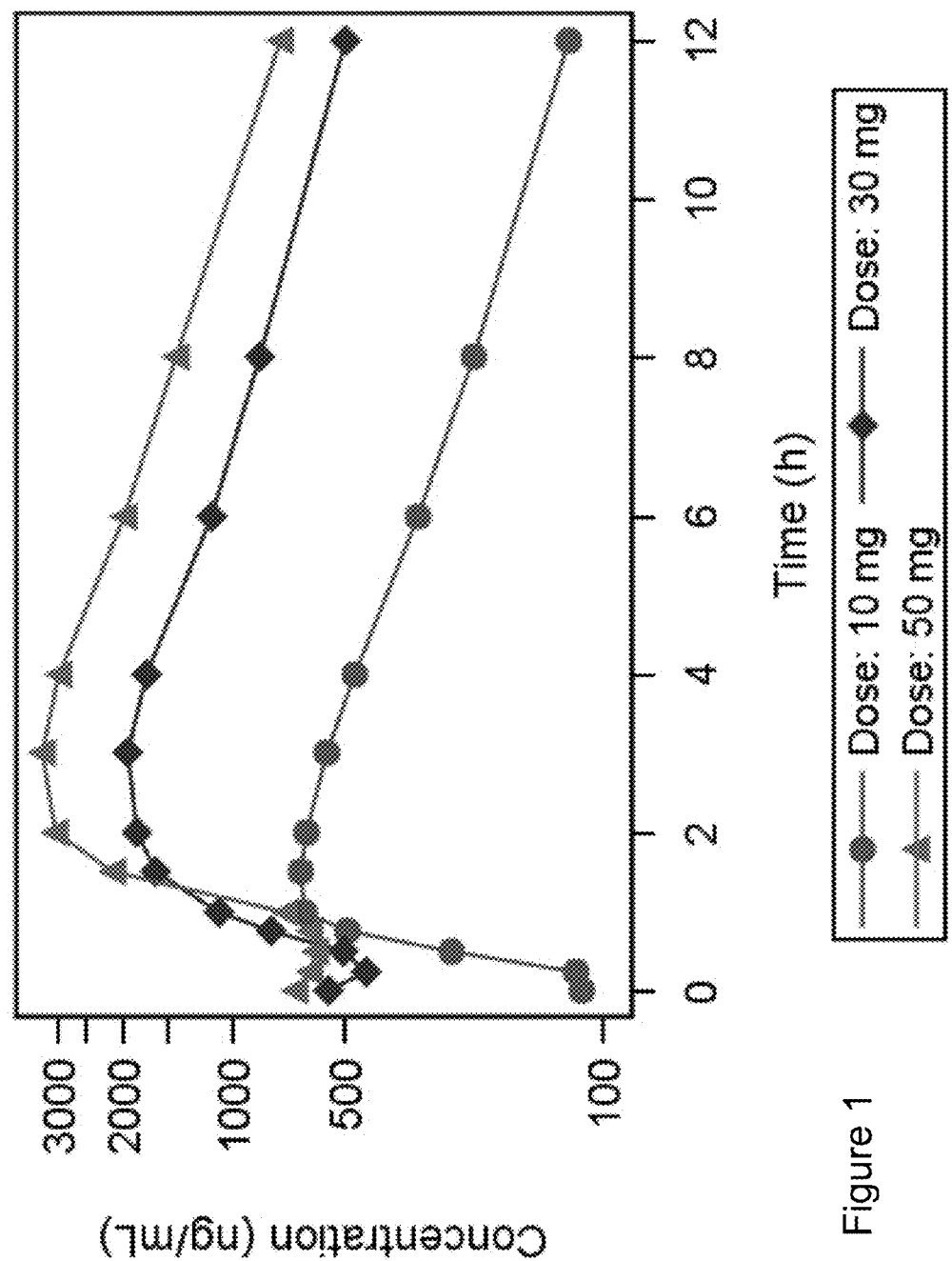
FIG. 1 shows mean plasma pemirolast concentrations (semi-log) versus time on Day 5 during a multiple-dose, open safety and tolerability study.

According to the invention, there is provided pemirolast, or a pharmaceutically acceptable salt thereof, for use in the treatment of airway hyperresponsiveness (hereinafter "AHR").

The term "AHR" will be understood to include the term bronchial hyperresponsiveness or hyperreactivity (BHR), and the characteristic feature of asthma that is found in almost every patient with the disease, as manifest by inter alia a measurably greater degree of tendency to airway constriction (following external stimuli or otherwise) than is typically exhibited in non-asthmatic patients.

Factors that contribute to AHR may thus be persistent or variable, relating to one or more of (i) structural differences manifest by changes altering the architecture of the airways in asthmatic patients making them thicker, less compliant and/or more narrowed than airways in non-asthmatic patients, and/or (ii) inflammatory events in the airway that are influenced by e.g. environmental factors, such as allergens, respiratory infections and medication. See, for example, Busse in *Chest*, 138 (Suppl.), 4S (2010).

AHR may alternatively be defined as being exhibited or diagnosed in patients following a standard bronchoprovocation test leading to bronchoconstriction, for example a direct inhalation challenge test, such as a methacholine challenge test (see, for example, the Busse reference supra (the disclosure in which document is hereby incorporated by reference)), or a histamine challenge test, or an indirect challenge test, using a stimulus such as exercise, dry air hyperpnea, distilled water, hypertonic saline or, more preferably, mannitol, in a mannitol challenge test, for example as described hereinafter and/or in the review article by Leuppi in *Curr. Opin. Pulm. Med.*, 20, 31 (2014) (the entire disclosure in which document is hereby incorporated by reference). AHR may be defined to be present when, having been subjected to such a test, a patient exhibits a $PD_{15}$ (i.e. a 15% fall in forced expiratory volume in one second ($FEV_1$)) at a cumulative dose of mannitol of no more than about 635 mg/mL, such as no more than about 475 mg/mL, including no more than about 315 mg/mL, e.g. no more than about 155 mg/mL, for example no more than about 75 (e.g. about 35, including about 15, such as about 5) mg/mL.

According to a second aspect of the invention there is provided a method of treatment of AHR, which method comprises the administration of a pharmacologically-effective amount of pemirolast, or a pharmaceutically acceptable salt thereof, to a patient in need of such treatment.

AHR may be considered to be an underlying feature of not just asthma, but also other conditions including chronic obstructive pulmonary disease (COPD), asthma-COPD overlap syndrome (ACOS), and idiopathic pulmonary fibrosis (IPF).

According to three further aspects of the invention, there is provided the treatment of AHR in:
(i) asthma patients;
(ii) COPD patients;
(iii) asthma-COPD overlap syndrome patients; and/or
(iv) IPF patients, which method comprises the administration of a pharmacologically-effective amount of pemirolast, or a pharmaceutically acceptable salt thereof, to a patient diagnosed with one or more of the relevant diseases, and therefore in need of such treatment.

As far as asthma is concerned, the treatment of AHR according to the present invention is not the same thing as normal, symptomatic asthma treatments discussed hereinbefore, whether by way of:

(a) daily prophylaxis of asthma (which makes airways less sensitive, reduces airway inflammation and/or dries up mucus), to prevent symptoms and/or asthma attacks (i.e. typical "preventer" medication as described hereinbefore); or (b) the therapeutic treatment of acute asthmatic episodes (asthma attacks) by way of bronchodilation (i.e. typical "reliever" medication as described hereinbefore).

It is rather, on at least a temporary basis, a non-symptomatic and/or a curative treatment of the underlying condition (asthma) itself, or, at a very minimum, a non-symptomatic and/or a curative treatment of the underlying bronchial hypersensitivity that is responsible for the condition, and the exhibition of the condition's symptoms in the first place. It is, in essence, on at least a short term basis, a "cure" for the asthma itself.

According to a further aspect of the invention there is provided a method of curative treatment of asthma, or the non-symptomatic treatment of asthma (as defined above), which method comprises the administration of a pharmacologically-effective amount of pemirolast, or a pharmaceutically acceptable salt thereof, to a patient in need of such treatment.

To the applicant's knowledge, nothing has ever been shown to have this effect previously, even on a short-term basis, based on a single dose of medication, and when drug is no longer present in the system.

"Patients" include mammalian (particularly human) patients.

The treatment of AHR according to the invention includes reducing AHR as manifest over the course of a treatment with pemirolast or a salt thereof by exhibiting a $PD_{15}$ in a standard mannitol challenge test, for example as described herein and/or in the review article by Leuppi in *Curr. Opin. Pulm. Med.*, 20, 31 (2014), at a cumulative dose of about 635 mg/mL or below.

According to a further aspect of the invention therefore, there is provided a method of reducing AHR in a patient, which method comprises:

(a) measuring $PD_{15}$ in a mannitol challenge test in that patient;

(b) determining whether that $PD_{15}$ is exhibited at a cumulative mannitol dose of no more than one of the values mentioned hereinbefore for that mannitol challenge test, and particularly no more than about 5 mg/mL, no more than about 15 mg/mL, no more than about 35 mg/mL, no more than about 75 mg/mL, no more than about 155 mg/mL, no more than about 315 mg/mL, no more than about 475 mg/mL, or no more than about 635 mg/mL; and (c) if so, administering pemirolast, or a pharmaceutically acceptable salt thereof, to that patient for a period of time, at an appropriate frequency and at an appropriate dosage (vide infra) to increase the cumulative dose at which $PD_{15}$ is exhibited, for example to above one of those relevant values, including those mentioned above or herein.

Pharmaceutically-acceptable salts of pemirolast that may be mentioned include acid addition salts and base addition salts. Such salts may be formed by conventional means, for example by reaction of a free acid or a free base form of an active ingredient with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of an active ingredient in the form of a salt with another counter-ion, for example using a suitable ion exchange resin.

Preferred salts of pemirolast include alkaline earth, and more particularly alkali, metal salts, such as calcium, magnesium, preferably potassium salts (e.g. pemirolast potassium) and sodium salts (e.g. pemirolast sodium hemihydrate, as described in international patent application WO 2010/146348).

In the uses and methods described herein, pemirolast and salts thereof are preferably administered locally or systemically, for example orally, intravenously or intraarterially (including by intravascular or other perivascular devices/dosage forms (e.g. stents)), intramuscularly, cutaneously, subcutaneously, transmucosally (e.g. sublingually or buccally), rectally, transdermally, nasally, pulmonarily (e.g. tracheally, bronchially or by inhalation), topically, or by any other parenteral route, in the form of a pharmaceutical preparation comprising the compound in a pharmaceutically acceptable dosage form. Preferred modes of delivery include oral, intravenous, cutaneous or subcutaneous, nasal, intramuscular, or intraperitoneal delivery.

Pemirolast and salts thereof will generally be administered in the form of one or more pharmaceutical formulations in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Such pharmaceutically acceptable carriers may also impart an immediate, or a modified, release of pemirolast/salt thereof.

Suitable pharmaceutical formulations may be commercially available or otherwise are described in the literature, for example, Remington *The Science and Practice of Pharmacy*, 19th ed., Mack Printing Company, Easton, Pa. (1995) and *Martindale—The Complete Drug Reference* (35$^{th}$ Edition) and the documents referred to therein, the relevant disclosures in all of which documents are hereby incorporated by reference. Otherwise, the preparation of suitable formulations may be achieved non-inventively by the skilled person using routine techniques.

Administration of pemirolast or salt thereof may be continuous or intermittent (e.g. by bolus injection). The mode of administration may also be determined by the timing and frequency of administration, but is also dependent, in the case of the treatment of AHR, on the severity of the condition. For example in the case of AHR in mild to moderate asthmatics, pemirolast may be administered perorally. In case of more severe asthmatics, pemirolast may be administered by inhalation or by bolus injection.

Similarly, the amount of pemirolast or salt thereof in the formulation will depend on the severity of the condition, and on the patient, to be treated, but may be determined by the skilled person.

However, as described hereinafter, we have found that pemirolast may be administered to humans at doses that are significantly higher than those presently employed in humans in the prevention of asthma, which doses are not only safe, but also give rise to the positive effect on the treatment of AHR. Accordingly, suitable lower daily doses (calculated as the free acid), irrespective of the route of administration, in adult patients (average weight e.g. 70 kg), may be about 110 mg, such as about 120 mg, for example about 125 mg, per day. Preferred lower daily doses (calculated as the free acid), irrespective of the route of administration, may be about 200 mg, such as about 300 mg, for example about 350 mg, including about 400 mg, per day. Doses may be split into two or more individual doses per day.

According to a further aspect of the invention there is provided pemirolast, or a pharmaceutically acceptable salt thereof, for use in the treatment of AHR, wherein pemirolast is administered at a dose of at least about 110 mg per day (calculated as the free acid). This corresponds to doses of about 1.5 mg/kg of body weight per day in all subjects irrespective of size or age.

Suitable upper limits of peroral daily dose ranges may be about 1,000 mg, such as about 800 mg, including about 600 mg, such as about 500 mg, for example about 400 mg, such as about 300 mg. Suitable upper limits for inhalation may be about 200 mg. Suitable upper limits for injectable bolus administration (e.g. subcutaneous or intravenous administration) may be about 5 g, for example about 2 g, such as about 0.8 g per day. (All of the above doses are calculated as the free acid and, again, doses may be split into two or more individual doses per day.)

In any event, the medical practitioner, or other skilled person, will be able to determine routinely the actual dosage, which will be most suitable for an individual patient, depending on the severity of the condition and route of administration. The above-mentioned dosages are exemplary of the average case; there can, of course, be individual instances where higher or lower dosage ranges are merited, and such are within the scope of this invention.

For example, calculated as the free acid, suitable lower dose limits are about 1.5 mg/kg of body weight per day (calculated as the free acid), irrespective of the mode of administration. Again, calculated as the free acid, suitable upper limits of peroral daily dose ranges may be about 15 mg/kg of body weight, for inhalation may be up to about 3 mg/kg of body weight; and for injectable bolus administration may be up to about 75 mg/kg of body weight.

Peroral and inhaled doses may be given between once and four times daily, preferably three times daily and more preferably twice daily. However, we have also found that high doses of pemirolast may be given less than once daily to treat AHR, such as every other day, every third day, or even weekly, two-weekly or three-weekly.

The dose administered to a mammal, particularly a human, in the context of the present invention should be sufficient to effect an appropriate response in the mammal (e.g. human) over a reasonable timeframe (as described hereinbefore). One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the age, condition, body weight, sex and response of the patient to be treated, and the stage/severity of the disease, as well as genetic differences between patients.

In the uses and methods described herein, pemirolast and pharmaceutically acceptable salts thereof may also be combined with one or more active ingredients that are useful in the treatment of asthma. Such patients may thus also (and/or already) be receiving such asthma therapy based upon administration of one or more of such active ingredients, by which we mean receiving a prescribed dose of one or more of those active ingredients mentioned herein, prior to, in addition to, and/or following, treatment with pemirolast or salt thereof.

Pharmaceutically-acceptable salts, and doses, of other active ingredients useful in the treatment of asthma include those that are known in the art and described for the drugs in question to in the medical literature, such as *Martindale—The Complete Drug Reference* (35$^{th}$ Edition) and the documents referred to therein, the relevant disclosures in all of which documents are hereby incorporated by reference.

Wherever the word "about" is employed herein, for example in the context of amounts (e.g. doses or concentrations of active ingredients), or time periods, it will be appreciated that such variables are approximate and as such may vary by ±10%, for example ±5% and preferably ±2% (e.g. ±1%) from the numbers specified herein.

The uses/methods described herein may have the advantage that, in the treatment of AHR, they may be more convenient for the physician and/or patient than, be more efficacious than, be less toxic than, have a broader range of activity than, be more potent than, produce fewer side effects than, or that it may have other useful pharmacological properties over, similar methods (treatments) known in the prior art.

EXAMPLES

Figure 2:
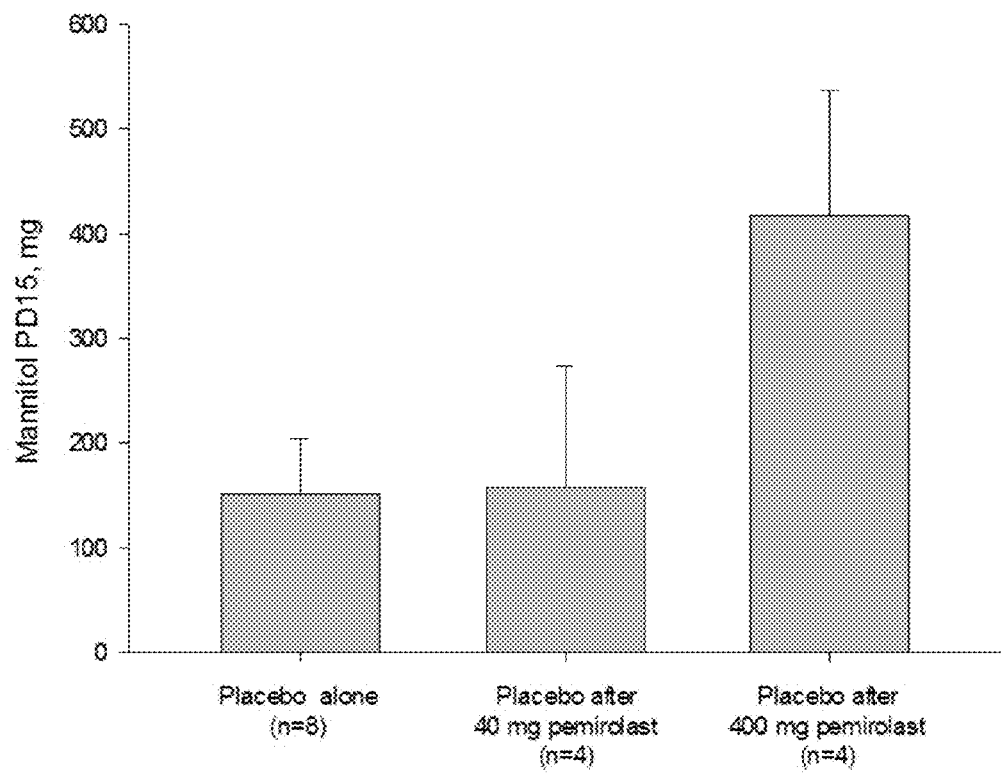
FIG. 2 shows back-transformed means and means+SEM for logged mannitol $PD_{15}$ for placebo treatments alone, preceded by a 40 mg dose of pemirolast, and preceded by a 400 mg dose of pemirolast.
Figure 3:
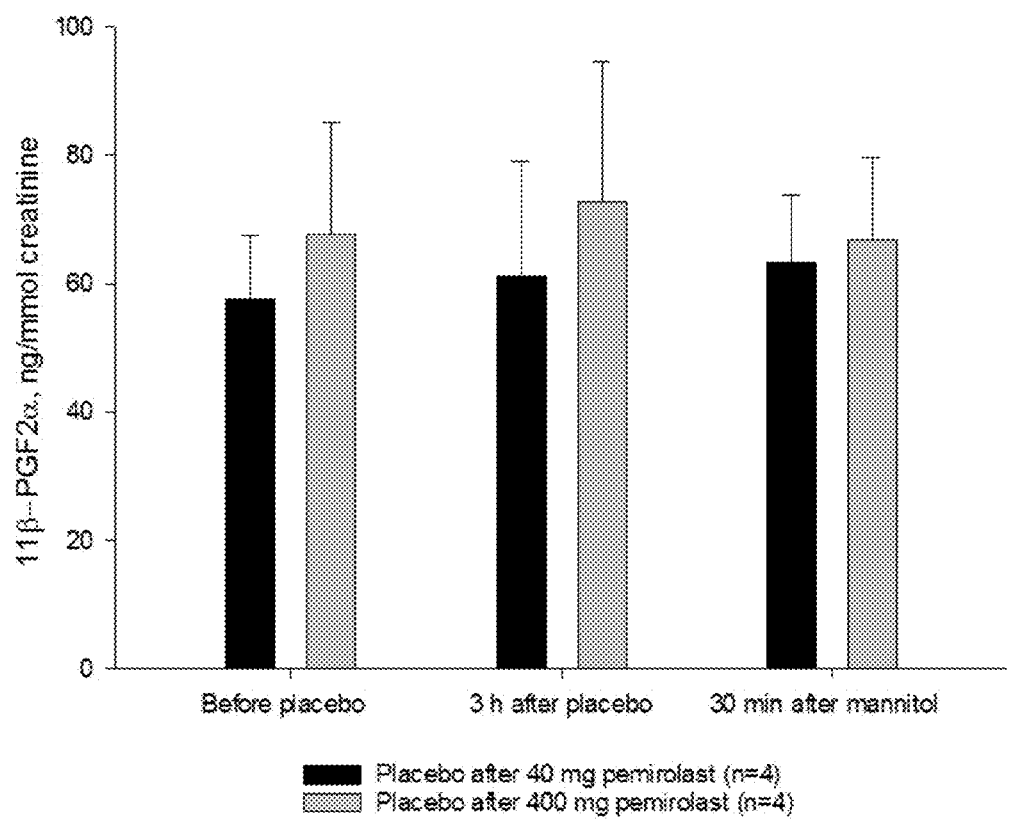
FIG. 3 shows levels of a PGD2 biomarker in urine as between patients treated (with reference to FIG. 2) with 40 mg and 400 mg.

The invention is illustrated, but in no way limited, by the accompanying Examples, which refer to accompanying FIGS. 1-3 as described herein.

Example 1

Pharmacokinetics of Pemirolast in Humans

This study comprised 18 healthy male subjects, 18-45 years of age, and was a single and multiple-dose, open study assessing the safety and tolerability of pemirolast potassium tablets (10 mg, Ulgixal™ tablets) with the doses 10, 30 and 50 mg (containing 8.5, 25.5 and 42.5 mg pemirolast free acid, respectively) b.i.d. (6 subjects in each dose group).

The subjects received a single dose on the first day, then b.i.d. for three days and a single dose on the fifth day. The study was performed at the Berzelius Clinical Research Center AB in Linköping, Sweden. All laboratory pharmacokinetic analyses were performed by Quintiles AB, Uppsala, Sweden. Pharmacokinetic calculations were performed by Pharm Assist Sweden AB, Uppsala, Sweden.

Mean $C_{max}$ data after multiple dosing are shown in and Table 1, and mean plasma concentrations over time on Day 5 are shown in FIG. 1.

TABLE 1

Multiple dose pharmacokinetics of orally administered pemirolast potassium; 10, 30 and 50 mg doses

| | | Dose | | |
|---|---|---|---|---|
| | | 10 mg (N = 6) | 30 mg (N = 6) | 50 mg (N = 6) |
| $C_{max}$ (µg/mL) | Mean | 0.73 | 2.04 | 3.42 |

Based on these clinical data, $C_{max}$ predictions were made (assumption: Linear pharmacokinetics when extrapolating to higher dose levels) and are presented in Table 2.

TABLE 2

$C_{max}$ Predictions

| Multiple dose | Exposure parameter | Value | Predicted values (mg) | | |
|---|---|---|---|---|---|
| | | | 125 | 200 | 400 |
| 8.5 mg | $C_{max}$ (µg/mL) | 0.73 | 10.68 | 17.08 | 34.16 |
| 25.5 mg | $C_{max}$ (µg/mL) | 2.04 | 9.98 | 15.98 | 31.95 |
| 42.5 mg | $C_{max}$ (µg/mL) | 3.42 | 10.07 | 16.12 | 32.23 |

Thus, multiple oral b.i.d. dosing with 125 mg pemirolast is predicted to result in plasma concentrations ($C_{max}$) of about 10 µg/ml. To the applicant's knowledge pharmacokinetics of multiple b.i.d. doses of 25.5 mg pemirolast (30 mg pemirolast potassium) or higher have not previously been studied in man.

Later pharmacokinetic studies in healthy volunteers (7 to 8 in each group) have shown that actual $C_{max}$ values for various multiple doses (b.i.d. for three and a half days) are as follows:
80 mg-8.84 µg/mL
200 mg-32.55 µg/mL
320 mg-50.95 µg/mL.
Pemirolast was found to be safe and well-tolerated at all of these doses.

Example 2

Toxicokinetics of Pemirolast in the Dog

In a study in the Beagles, systemic pemirolast exposure was determined for orally administered pemirolast potassium at 75 mg/kg daily for 7 consecutive days in male and female dogs (75 mg/kg daily having been found to be a safe chronic dose in dogs). The study, including all analyses and calculations, were performed by WIL Research, France, in compliance with Good Laboratory Practices (GLP).

There were no major differences in kinetics between males and females. Mean $C_{max}$ is shown in Table 3.

TABLE 3

| | 75 mg/kg repeated dose (7th day) | |
|---|---|---|
| Variables | Males (n = 3) | Females (n = 3) |
| $C_{max}$ (µg/mL) | 168 | 150 |

Example 3

Effect of Pemirolast of hERG Channels

This study was performed by PhysioStim, France, a GLP compliant facility.

The effects of pemirolast on hERG currents in HEK-293 cells stably expressing the hERG potassium channel were studied using patch-clamp technique. In these experiments, 2.7, 8.0, 26.6 and 79.9 μg/mL of pemirolast potassium concentration-dependently decreased hERG tail current amplitude by 5.4%, 10.2%, 14.1% and 19.0%, respectively.

The reference compound E-4031 (0.1 μmol/L), a selective hERG inhibitor, reduced hERG tail current amplitude by 82.0%, thus confirming the pharmacological sensitivity of the hERG potassium channel in these experiments. In conclusion, $IC_{50}$ for pemirolast could not be calculated because the inhibition was less than 20% at the highest concentration tested.

These results show that pemirolast lacks potential to inhibit hERG channel (an important human "anti-target" that must be avoided during drug development to reduce the risk of certain potentially fatal cardiac adverse effects) at concentrations up to about 80 μg/mL.

Example 4

Clinical Trial

This study comprised male and female asthma patients (18 to 46 years of age) with a positive asthma test (as determined by a mannitol challenge test (vide infra) performed within 15 days prior to enrolment at the first screening visit, Visit 1).

At entry, about 20% of the patients had ongoing asthma treatment with long-acting beta2-agonists (LABA), and about 40% of the patients had ongoing asthma treatment with inhaled glucocorticosteroids (ICS).

It was a double-blind, randomized, placebo-controlled, cross-over trial assessing the efficacy of orally administered single doses of placebo and 40 mg and 400 mg of pemirolast (immediate release tablets containing pemirolast sodium hemihydrate, as well as microcrystalline cellulose, mannitol, copovidone fine, croscarmellose sodium, anhydrous colloidal silica and magnesium stearate) in patients challenged with mannitol inhalation as described below.

The patients were exposed to the different treatments at three separate hospital visits at least 2 (mean 6.8, median 6) days apart. The data reported in FIGS. 2 and 3 below represent the patients that received placebo treatment at the first visit (n=8) or placebo at the second visit (after 40 mg at the first visit (n=4) or after 400 mg at the first visit (n=4)).

All doses were administered 3 hours before initiation of the mannitol challenge test to ensure peak plasma concentrations of pemirolast when the mannitol challenge was performed (blood samples for analysing plasma concentrations of pemirolast were collected 3 hours after drug administration).

There were 5 visits during the trial: A screening visit (Visit 1, within 15 days before Visit 2), three visits for treatment with Investigational Medicinal Products (IMP; pemirolast 40 or 400 mg, or placebo) (Visit 2-4, spaced at least 2 days apart), and a final follow-up visit by telephone (Visit 5, at least 2, but less than 4 days after Visit 4 and within 30 days of Visit 2).

All laboratory pharmacokinetic analyses were performed by Clinical Pharmacology, Karolinska University Hospital, Stockholm, Sweden. Briefly, the concentration of pemirolast in human plasma was determined by solid phase extraction and liquid chromatography followed by tandem mass spectrometric detection (LC-MS/MS). The analytical method, utilizing a 200 μL sample aliquot, has a calibration range of 4.00-4000 ng/mL, with a lower limit of quantification (LLOQ) set at 4.00 ng/mL.

At Clinical Pharmacology the method has earlier been partially validated prior to sample analysis.

The trial was performed in compliance with Good Clinical Practice (GCP).

Inclusion Criteria were:
Written informed consent before the trial
Age ≥18 and <50 years
Diagnosis of asthma according to Global Initiative for Asthma (GINA) Guidelines
Fractional exhaled nitric oxide (FENO) >20 ppb (calculated average of 2 independent FENO measurements)
Baseline FEV1 >80% of the predicted normal value at Visit 1
Demonstration of PD15 at ≤315 mg mannitol Exclusion Criteria were:
Lower respiratory tract infection <6 weeks prior to the trial
Influenza vaccination <4 weeks prior to the trial
Current smokers
Ex-smokers with a smoking history of >10 pack years (e.g. 10 pack years=1 pack/day×10 years, or ½ pack/day×20 years). An ex-smoker may be defined as a subject who has not smoked for >6 months prior to the trial
Treatment with any of the medications listed below <3 weeks prior to the trial:
  Inhaled steroids in a dose equivalent to >2×400 μg budesonide/day (dose must not be changed <4 weeks prior to and during the trial)
  Oral corticosteroids
  Any systemic immunomodulatory therapy
  Any systemic anti-rheumatic therapy
  Anti-IL-4 therapy
  Clinically significant comorbidities that may be compromised by induced bronchospasm or repeated spirometry as judged by Investigator
BMI >30
Known HIV positive
Known active hepatitis B or C
Significant concurrent, uncontrolled medical condition including, but not limited to, renal, hepatic, cardiac, haematological, gastrointestinal, endocrine, inflammatory, autoimmune, pulmonary, neurological, cerebral or psychiatric disease evaluated by the Investigator to interfere with effect of the trial drug
Subjects who have a clinically significant abnormal laboratory value and would be at potential risk if enrolled in the trial as evaluated by the Investigator
Known uncontrolled allergic conditions or allergy/hypersensitivity to any component of the trial drug or placebo excipients
Known uncontrolled allergic conditions or allergy/hypersensitivity to mannitol or gelatine used to make capsules
Breast-feeding female subjects
Female subjects of childbearing potential not willing to use adequate contraceptive methods (adequate contraceptive measures as required by local requirements or practice) during participation in the trial until at least 3 days after last intake of investigational drug
Male subjects not surgically sterilized, who or whose partner is not using adequate contraceptive methods (adequate contraceptive measures as required by local requirements or practice) during participation in the trial until at least 3 days after last intake of investigational drug
Receipt of any experimental agents within 30 days prior to the trial
Participation in any other interventional clinical trial during the trial period Subjects known or suspected of not being able to comply with the trial protocol (e.g. due to alcoholism, drug dependency or psychological disorder)

The primary endpoint in the study was the Provocation Dose (PD) of mannitol resulting in a 15% fall in Forced Expiratory Volume during 1 second (FEV1; values given in Liters (L)) ($PD_{15}$ for mannitol), which is recognised by regulatory authorities as an acceptable method to evaluate potential efficacy of asthma drugs (*European Medicines Agency. Note for Guidance on Clinical Investigation of Medicinal Products for Treatment of Asthma*, 2013).

The mannitol challenge test (Aridol®, Pharmaxis Ltd, Frenchs Forest, Sydney Australia) was performed as follows: Application of nose clip and challenge with 0 (empty capsule acting as placebo), 5, 10, 20, 40, 80, 160, 160, 160 and 160 mg of mannitol via the Halermatic (the 80 and 160 mg doses were given as multiple doses of 40 mg capsules). After inhalation, subjects were instructed to hold their breath for 5 seconds.

At least 2 repeatable FEV1 manoeuvres were performed 60 seconds after each dose and the highest FEV1 was used in the calculation. The FEV1 value taken after the 0 mg capsule was taken as pre-challenge FEV1 and used to calculate the percentage decrease in FEV1 in response to the mannitol challenge. The test was ended when the FEV1 had fallen by 15% or more. The mannitol PD15 in the trial participants ≤15 days before the first drug treatment was 133 mg (Geometric mean, n=24).

A secondary endpoint in the study was to analyse changes in urinary excretion of a metabolite (11β-prostaglandin (PG) F2α) of the lung mast cell mediator/biomarker prostaglandin D2. 11β-PGF2α analysis was performed in unextracted urine samples using a validated enzyme immunoassays (EIA) kit from Cayman Chemical, Ann Arbor, Mich., USA (Item no 516521). Absolute values of the mediators were expressed as nanograms 11β-PGF2α per millimole creatinine.

At the days of treatment with IMP (pemirolast 40 or 400 mg, or placebo), and mannitol testing (Visit 2-4), the following procedure was followed:
1) Before IMP administration testing:
   a) Withdrawal from trial visit criteria to be checked
   b) Urine sampling for 11β-PGF2α analysis
   c) Blood sampling for haematology and blood biochemistry
   d) Vital signs, physical examination, adverse events and concomitant medication
2) Administration of IMP 3 hours (+/−10 min) before the mannitol challenge
3) Before mannitol challenge:
   a) <10 min before: Urine sampling for 11β-PGF2α analysis
   b) <10 min before: Blood sampling for analysis of plasma pemirolast concentration
4) Mannitol test 3 hours (+1-10 min) after IMP administration
5) After mannitol challenge:
   a) Urine sampling for 11β-PGF2α, 30 minutes after mannitol challenge
   b) Pregnancy test (Visit 4 only, in addition to prior to enrolment)
   e) Recording of concomitant medication just before sending the patient home
   f) Reporting of AEs just before sending the subject home The following treatments were not allowed from ≤3 weeks prior to the screening visit (Visit 1) and during the trial period:
   Inhaled steroids in a dose equivalent to >2×400 µg budesonide per day (dose must not be changed <6 weeks prior to Visit 1 and during the study)
   Oral corticosteroids
   Any systemic immunomodulatory therapy
   Any systemic anti-rheumatic therapy
   Anti-IL-4 therapy The following treatments were not allowed within the indicated time-frames:

| Time to withhold before mannitol challenge test was performed | Medication |
|---|---|
| 6-8 hours | Inhaled non-steroidal anti-inflammatory agents |
| 8 hours | Short acting $Beta_2$ agonists |
| 12 hours | Short-acting anticholinergic |
| 24 hours | Inhaled corticosteroids plus long-acting $Beta_2$ agonists |
| 24 hours | Long acting $Beta_2$ agonists |
| 72 hours | Antihistamines |
| 72 hours | Long-acting anticholinergic |
| 4 days | Leukotriene receptor antagonists |

Results

The results of the study showed that 3 hour pre-treatment with pemirolast increased the mannitol $PD_{15}$.

An unexpected and surprising finding in this study was that 400 mg, but not 40 mg, of pemirolast p.o. resulted in a "curative" anti-asthma effect that persisted beyond the elimination of pemirolast from circulation.

As shown in FIG. 2, placebo-treated patients tolerated a much higher dose of mannitol when a single 400 mg dose of pemirolast was given at least 3 days before placebo/mannitol. Such a reduction in airway/bronchial hyper-responsiveness/reactivity (AHR/BHR) was not seen when the placebo treatment was preceded by a pemirolast dose of 40 mg.

The mean peak plasma concentrations of pemirolast 3 hours after the 40 and 400 mg doses have been found to be about 3,000 ng/mL and 35,000 ng/mL (with $t_{1/2}$ being about 4 to 7 hours), respectively (geometric mean values, n=23-24).

In all three experimental placebo groups presented in FIG. 2, the mean plasma concentrations of pemirolast were below the limit of quantification of the analytical method (4 ng/mL), and there were no relevant differences between the groups.

Treatment with 400 mg pemirolast for 3 hours did not per se increase FEV1 which was 3.58±0.86 L before treatment and 3.55±0.84 L 3 hours after an oral dose of 400 mg pemirolast (mean values ±SD, n=22). This finding suggests that the lasting effect of pemirolast was not a result of a baseline bronchodilatory effect of pemirolast.

Furthermore, the long-lasting reduction of AHR/BHR to mannitol challenge by the 400 mg dose of pemirolast did not seem related to inhibition of mast cells.

Prostaglandin D2 (PGD2) is released from mast cells (e.g. in the lung) and is known as a mediator of asthmatic bronchoconstriction (Hardy et al, *N. Engl. J. Med.*, 311, 209 (1984)). Urinary levels of the PGD2 metabolite 11β-PGF2α increase acutely during asthmatic attacks, including those induced by mannitol inhalation (Brannan et al, *Eur. Respir. J.*, 22, 491 (2003)). This PGD2 metabolite is therefore used as a biomarker for mast cell activation in asthmatics.

Urinary levels of the PGD2 biomarker in urine did not differ between the patients that had previously (at least 3 days before) been treated with 40 mg or 400 mg (FIG. 3, same 4+4 patients as in FIG. 2). If anything, the levels of the mast cell biomarker tended to be slightly higher with the 400 mg dose than the 40 mg dose.

In this study, there were no serious adverse events or clinically significant changes in vital signs, findings at physical examination or in haematological or blood biochemistry laboratory tests.

Taken together, a dose of pemirolast higher than ever previously tested in asthmatics, causes an unexpected curative anti-asthma effect (measured as a reduced AHR/BHR to mannitol) that persists after the drug is cleared from the circulation and appears to be unrelated to inhibition of mast cells and direct bronchodilatory effects.

The invention claimed is:

1. A method for the treatment of airway hyperresponsiveness, which method comprises:
    administering pemirolast, or a pharmaceutically acceptable salt thereof, to a human patient having a condition characterized by airway hyperresponsiveness, wherein said administering is carried out by orally administering a dose effective to reduce airway hyperresponsiveness, which dose is at least about 350 mg per day.

2. A method as claimed in claim 1, wherein the condition is asthma.

3. A method as claimed in claim 1, wherein the condition is chronic obstructive pulmonary disease.

4. A method as claimed in claim 1, wherein the condition is asthma-chronic obstructive pulmonary disease overlap syndrome.

5. A method as claimed in claim 1, wherein the condition is idiopathic pulmonary fibrosis.

6. The method according to claim 1, wherein the dose is between about 350 and about 600 mg per day.

7. A method as claimed in claim 1, wherein the human patient is receiving an additional agent selected from the group consisting of a long-acting bronchodilator, theophylline, a corticosteroid, a leukotriene modifier, a cromone, an anti-IgE antibody, a beta-agonist, and an anticholinergic agent.

\* \* \* \* \*